United States Patent
Friedman et al.

(10) Patent No.: US 6,666,833 B1
(45) Date of Patent: Dec. 23, 2003

(54) SYSTEMS AND METHODS FOR FOCUSSING AN ACOUSTIC ENERGY BEAM TRANSMITTED THROUGH NON-UNIFORM TISSUE MEDIUM

(75) Inventors: Zvi Friedman, Qiriat Bialik (IL); Dov Maor, Haifa (IL)

(73) Assignee: Insightec-TxSonics Ltd, Tirat Carmel (IL)

(*) Notice: Subject to any disclaimer, the term of this patent is extended or adjusted under 35 U.S.C. 154(b) by 353 days.

(21) Appl. No.: 09/724,817

(22) Filed: Nov. 28, 2000

(51) Int. Cl.⁷ .............................. A61H 1/00; A61H 1/02; A61H 5/00
(52) U.S. Cl. .......................... 601/2; 600/407; 600/437; 600/439
(58) Field of Search .............................. 601/2; 600/407, 600/437, 439

(56) References Cited

U.S. PATENT DOCUMENTS

| | | | |
|---|---|---|---|
| 4,233,988 A | * 11/1980 | Dick et al. | 128/660 |
| 4,509,526 A | * 4/1985 | Barnes et al. | 128/663 |
| 5,111,822 A | * 5/1992 | Dory | 128/660.03 |
| 5,590,657 A | * 1/1997 | Cain et al. | 128/660.03 |
| 5,613,940 A | 3/1997 | Romano | |
| 6,217,508 B1 | * 4/2001 | Ball et al. | 600/25 |

OTHER PUBLICATIONS

Lars A. Odegaard, Using Signals Scattered From Diffuse Inhomogeneities to Correct for Phase Aberrations Caused by a Phase-Screen Far From the Transducer, 1995 IEEE Ultrasonics Symposium –XP–000628755; 0–7803–2940–6/95/ $4.00, Pub. Date: Jul. 11, 1995. pp 1443–1447.

* cited by examiner

Primary Examiner—Henry Bennett
Assistant Examiner—Sabrina Dagostino
(74) Attorney, Agent, or Firm—Bingham McCutchen LLP

(57) ABSTRACT

Systems and methods for focussing an ultrasound energy beam transmitted from an array of transducer elements located outside the body through a non-uniform tissue medium, such as a skull, to a location (e.g., a tumor) located inside the body by monitoring a signal representing reflected portions of the beam at a desired focal point or zone through a portion of the medium that does not significantly distort the reflected signal. In one embodiment, a focussed ultrasound system includes a plurality of transmitting transducer elements configured to deliver respective energy waves from locations outside the skull to a focal zone within the skull, the energy waves collectively comprising an energy beam. The system further includes an ultrasound detector having a fixed position relative to the transmitting elements, the detector configured to receive a signal comprising a reflected portion of the beam along a line-of-sight axis through a portion of the skull. A controller is coupled to the transmitter and detector, the controller configured to calculate the intensity of the reflected portion of the beam along the axis based on the timing of the received signal and then adjust the transmission of one or more of the transmitting elements based on the calculated intensity of the reflected portion of the beam along the axis.

11 Claims, 3 Drawing Sheets

SYSTEMS AND METHODS FOR FOCUSSING AN ACOUSTIC ENERGY BEAM TRANSMITTED THROUGH NON-UNIFORM TISSUE MEDIUM

FIELD OF INVENTION

The present invention relates generally to thermal energy treatment systems, such as MRI-guided focused ultrasound systems and, more particularly, to systems and methods for focussing an acoustic energy beam transmitted through non-uniform tissue.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors, thereby eliminating the need for invasive surgery. For this purpose, focused ultrasound systems having piezoelectric transducers driven by electric signals to produce ultrasonic energy have been employed.

In such systems, such as a MRI-guided focused ultrasound system, the transducer is positioned external to the patient, but in generally close proximity to a target tissue region within the patient to be ablated. The transducer may be geometrically shaped and positioned so that the ultrasonic energy is focused at a "focal zone" corresponding to the target tissue region, heating the region until the tissue is necrosed. The transducer may be sequentially focused and activated at a number of focal zones in close proximity to one another. For example, this series of "sonications" may be used to cause coagulation necrosis of an entire tissue structure, such as a tumor, of a desired size and shape.

A spherical cap transducer array, such as that disclosed in U.S. Pat. No. 4,865,042 issued to Umemura et al., has been suggested for this purpose. This spherical cap transducer array includes a plurality of concentric rings disposed on a curved surface having a radius of curvature defining a portion of a sphere. The concentric rings generally have equal surface areas and may also be divided circumferentially into a plurality of curved transducer elements or sectors, creating a tiling of the transducer face. The transducer elements are driven by radio frequency (RF) electrical signals at a single frequency offset in phase and/or amplitude. The phase and amplitude of the respective drive signals may be individually controlled such that a "focal zone" of the emitted ultrasonic energy has a desired distance, shape, orientation and energy level in the target tissue region.

For example, if all of the sectors are driven by drive signals that are in phase with one another, the ultrasonic energy will be focused substantially at a relatively narrow focal zone. Alternatively, the sectors may be driven with respective drive signals that are in a predetermined phase relationship with one another. The discrete nature of the phase differences among the sectors results in a number of zones that collectively define a wider area of focus and cause necrosis of a larger tissue region within a focal plane intersecting the focal zone. For example, these zones may collectively define an annulus surrounding a central zone.

More advanced techniques for obtaining specific focal distances, shapes and/or orientations are disclosed in U.S. patent application Ser. No. 09/626,176, filed Jul. 27, 2000, entitled "Systems and Methods for Controlling Distribution of Acoustic Energy Around a Focal Point Using a Focused Ultrasound System;" U.S. patent application Ser. No. 09/556,095, filed Apr. 21, 2000, entitled "Systems and Methods for Reducing Secondary Hot Spots in a Phased Array Focused Ultrasound System;" and U.S. patent application Ser. No. 09/557,078, filed Apr. 21, 2000, entitled "Systems and Methods for Creating Longer Necrosed Volumes Using a Phased Array Focused Ultrasound System." The foregoing applications, along with U.S. Pat. No. 4,865,042, are all hereby incorporated by reference for all they teach and disclose.

Such high frequency focused ultrasound systems may be employed in various parts of the body. Notably, when using high frequency focused ultrasound "energy beam" to thermally treat a certain area of the body, e.g., to ablate a tumor, the energy beam must be precisely focussed to the target location so as to avoid harming healthy tissue surrounding the target. As used herein, the terms "beam," "energy beam," or "acoustic energy beam" are used to refer generally to the wave sum of the waves emitted from the various transmitting elements of a focused ultrasound system. This focus is achieved by adjusting the phases and amplitudes of the individual waves to produce constructive interference at a particular location.

Towards this end, problems may be encountered when using a focussed ultrasound energy beam to treat a certain portion of the body in which the individual waves forming the beam must be transmitted through a non-uniform tissue medium, such as, e.g., the skull, the inner surface of which can be highly irregular in shape. This non-uniformity of the particular tissue medium introduces differential phase errors or phase aberrations in the respective ultrasound waves transmitted by transducer elements located at different places on the exterior of the body. For example, because the speed of sound is faster in bone than in tissue, the phase of a wave that passes through bone is advanced relative to one that passes through tissue. The relative amount of phase change depends on the thickness and consistency of the bone through which the individual waves are propagated. If the transmission paths of some transducer elements must travel through more or less bone medium than others, there is no total constructive interference of the waves at the intended focal zone, i.e., the beam is not well-focussed. Also, the different wave paths will usually cause different attenuation and, thus, the relative amplitudes of the individual waves will also not be optimal for creating the required focused interference pattern.

By way of another example, the speed of sound in fat tissue differs by about 7% from the speed of sound in muscle. If the target focal zone is underlying a non-uniform fat layer, this non-uniformity can cause phase aberrations in the individually transmitted waves, again depending on their respective transmission paths. Depending on the frequency of the waves, the aberrations. For example, at 1 MHz, a difference of one centimeter in the fat layer thickness in the transmission path of two different transmitting elements results in a phase difference of about 180°.

Notably, in a phased array ultrasound transmitting system, phase adjustments to individual transmitting elements can be made to compensate for the distortions caused- by transmission through a non-uniform tissue medium. Of course, this is only if the amount of phase shift needed for each respective transmitting element is known. A relatively accurate determination of the necessary phase corrections is possible in a closed loop fashion, by observing the beam intensity and adjusting the phases of the transmissions in order to maximize the beam intensity at a chosen point. To be able to focus the beam in the brain, however, one must be able to "see"

inside the patient's skull to determine whether or not the beam is focussed.

One such "closed-loop" approach is to employ a strong point reflector in the target tissue region to reflect energy pulses from the beam back to fixed detection elements, so that the system can determine if the energy pulses were applied to the correct location. With this approach, focussing of the beam would be achieved by measuring the roundtrip time it takes energy pulses from each beam element to travel out of the beam element to the reflector and back to the system detector. Alternatively, the reflection of the entire transducer array from the reflector could be maximized. However, such a point reflector does not normally exist within the target tissue region and invasive surgery would be required for its placement. For example, one prior art approach for focussing in the brain requires that a reflector be inserted into the brain and is based on time-reversal concepts. See, e.g., U.S. Pat. Nos. 5,431,053; 5,428,999; 5,276,654; 5,092,336; and 5,010,885. Of course, the physical insertion of a reflector into the skull or brain (or most any other region of the body, for that matter) is highly invasive and undesirable.

It is significant to implementing these focal positioning and shaping techniques to provide a transducer control system that allows the phase of each transducer element to be independently controlled. To provide for precise positioning and dynamic movement and reshaping of the focal zone, it is desirable to be able to change the phase of individual elements, e.g., in the $\mu$ second range. Notably, in a MRI-guided focused ultrasound system, it is desirable to operate the ultrasound transducer array without creating electrical noise or fields that interfere with the magnetic fields or gradients. Thus, it would be desirable to be able to obtain the required phase shifts for each transmitting element in the phased array, and then implement those phase shifts, in order to more precisely focus the beam at a desired location in the body requiring transmission through a non-uniform tissue medium, without needing to introduce a detector into the target site.

SUMMARY OF THE INVENTION

Various aspects of the present invention can be found in a system and methods of its use for directing and focussing an acoustic energy beam transmitted from a plurality of elements located outside a patient's body to a desired target location in the body underlying a non-uniform tissue medium, such as a skull, by monitoring a signal representing the intensity of a reflected portion the beam.

In one embodiment, a system for focussing an ultrasound beam transmitted from a phased array ultrasound transducer through a patient's skull includes an ultrasound detector focussed to receive a signal representative of the intensity of reflected portions of the beam through a portion of the intended focal zone. The detector is fixed in a known position relative to the transmitting elements of the transducer array and is preferably located at an acoustic window portion of the skull, such as, e.g., the eyes or temples, where there is little distortion of the received signal. Alternately, the detector may be located at a portion of the skull, which distorts the signal in a known, predictable and calculable manner. In particular, the detector is focussed along a line-of-sight axis passing through the intended focal zone. By monitoring the intensity of reflected portions of the beam along a line-of-sight through the focal zone, the system is able to adjust the phasing pattern and/or amplitude of the emitted signal of the transducer elements in order to better focus the beam, regardless of the particular distortion pattern caused by the patient's skull.

Other aspects, advantages and novel features of the present invention will become apparent from the following Detailed Description of Preferred Embodiments, when considered in conjunction with the accompanying drawings.

BRIEF DESCRIPTION OF THE DRAWINGS

The drawings illustrate both the design and utility of preferred embodiments of the present invention, wherein.

DETAILED DESCRIPTION OF PREFERRED EMBODIMENTS

Figure 1:
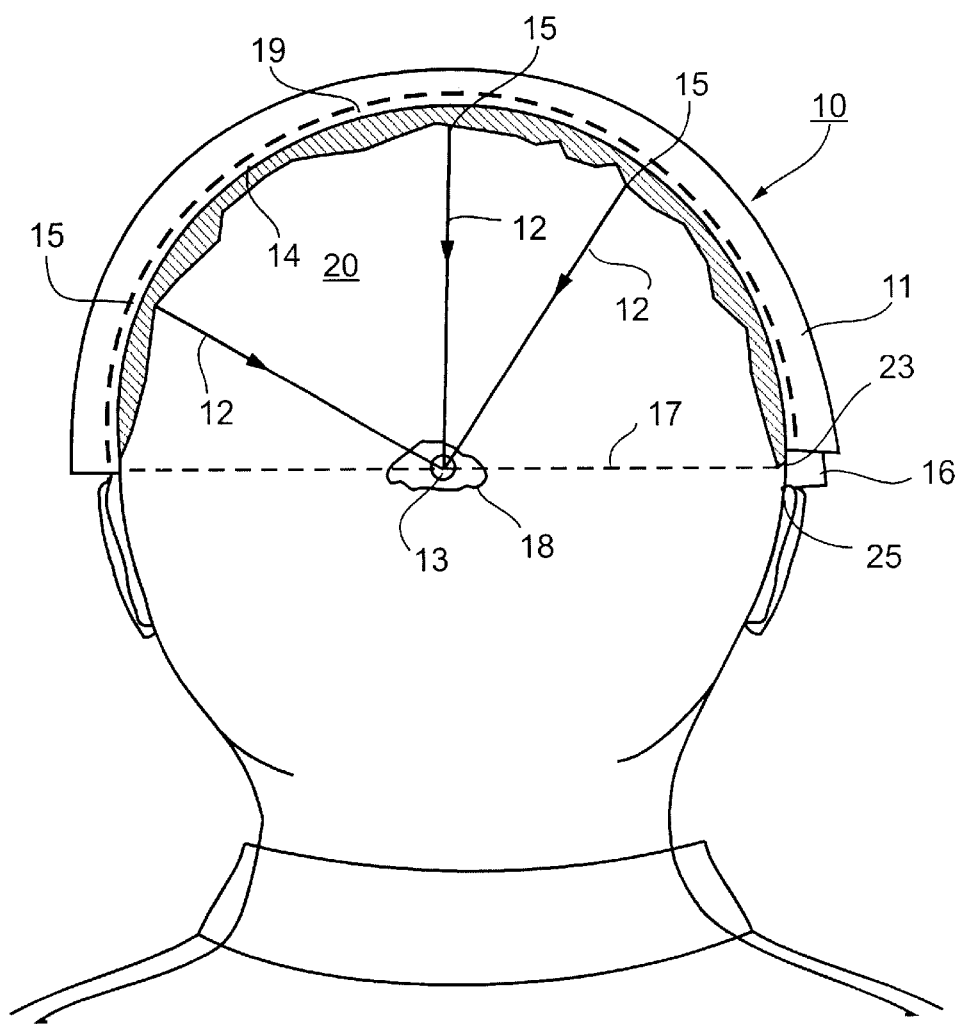
FIG. 1 is a cross-sectional view of a system for delivering a focused ultrasound energy beam inside a skull and detecting the intensity of reflected portions of the beam along an axis through an intended focal zone.

Referring to FIG. 1, an exemplary trans-cranial focussed ultrasound system 10 includes a high intensity focussed ultrasound transducer 11 shaped to conform generally to the exterior of a patient's skull 14. The transducer 11 comprises a phased array of individually controllable transducer elements 15, each configured to transmit acoustic wave energy through the patient's skull 14 to a target focal zone 13 in the patient's brain 20, the collective wave energy forming an energy beam 12. In accordance with known phased-array transmission techniques, the acoustic wave energy transmitted from each individual transducer element 15 may be offset in phase and/or amplitude from the others in order to change the location, shape and/or orientation of the focal zone 13. An acoustically conductive fluid or gel 19 is preferably introduced between the inner face of the transducer 11 and the exterior of the patient's skull 14 in order to prevent any acoustically reflecting air gaps. The system 10 may be operated in continuous mode, where the transducer elements 15 are continuously energized, pulsed mode, where the transducer elements 15 are periodically energized at a selected duty cycle, or in some selected sequence of both continuous and pulsed mode operation.

As described above, prior to initiating any high intensity beam transmission to a desired focal zone 13, the respective phase shifts and amplitudes of the individual transducer elements 15 must be properly adjusted (or "calibrated") to account for any aberrations in thickness of the skull 14. If properly focussed, the energy waves will converge at the focal zone 13 in phase, creating a constructive interference pattern with most all of the beam energy concentrated in the focal zone 13. However, if the phase shifts and/or amplitudes of the individual transducer elements 15 are not properly calibrated to account for the skull thickness aberrations, the energy beam 12 will be "defocused," appearing as a larger volume of non-uniform intensity 18.

Focussing of the beam 12 is preferably performed at low energy levels, so as to avoid harming any brain tissue before the beam 12 is properly focussed. Further, the focussing process is preferably performed after an initial approximation of the phase shifts of the individual transducer elements 15 is determined. A first approximation of the necessary phase corrections may be produced in an open loop fashion, e.g., from a CT scan image of the skull, taught in U.S. Provisional Patent Application Serial No. 60/253,955, entitled, "Open Loop Focussing For Ultrasound Therapy", filed on this same date, which is fully incorporated by reference.

In order to focus the energy beam 12 and, in particular, calibrate the phase shift and amplitude of the waves transmitted from the individual transducer elements 15, the system 10 employs an ultrasound signal detection probe 16 incorporating a detector transducer 23.

Notably, alternate embodiments may employ more than one detector transducer. The detector 23 is positioned in a fixed coordinate position relative to the transmitting transducer elements 15, and is "focussed" in the direction of the phased-array transducer focal zone 13. More particularly, the detector 23 has a relatively long and narrow focal volume, i.e., practically a line or very thin tube, such that its cross-section passing through the intended focal zone 13 of the phased-array transducer may be as small as 1 mm. In this manner, the detector 23 will receive reflections of the beam 12 transmitted through the skull from points along a relatively well defined axis 17, which passes through the intended transducer focal zone 13.

Notably, the transmitting transducer elements 15 emit acoustic waves (collectively forming the energy beam 12) at a base frequency. If the beam 12 is sufficiently intense, the tissue of the brain creates components of the beam 12 that are two, three, or more times the base frequency. Thus, for example, the transmit frequency of the beam 12 could be 800 kHz, and the receive frequency at the detection probe 16 could be 2,400 kHz. The intensity of these higher frequency components is a non-linear function of the base intensity.

In particular, the intensities of the higher harmonics are much weaker than that of the base frequency and, the higher the harmonic, the weaker the signal. However, the intensity of an harmonic has more than a linear relationship to the intensity of the base frequency, i.e. if the base intensity at one point is x times (x>1) higher than at another point, the intensity of the harmonics at the first point will be even larger than x times the intensity at the second point. Moreover, the higher the harmonic, the stronger this effect. The result is that, by employing a detector 23 sensitive enough to detect the relatively weak intensity of the higher harmonics, the contrast from one point to another will be strongly enhanced. Thus, as explained in greater detail herein, detection of these higher frequencies by the detector 23 provides a more sensitive measure of the intensity of the reflected signal, and ensures a better and faster convergence of the focussing process.

Preferably, the line-of-sight axis 17 of the detector 23 passes through an "acoustic window" 25 of the skull 14. As used herein, the term "acoustic window" is used to describe an area in the skull 14 that does not significantly distort the reflected portions of the beam 12 sensed by the detector 23. Such acoustic windows of the skull 14 will typically include the temples, eyes and portions of the base of the skull at the back of the neck. Alternately, the detector line-of-sight axis 17 may pass through a relatively thick portion of the patient's skull, so long as the particular thickness and, thus, the corresponding distortion, are known and can be compensated for.

Figure 2:
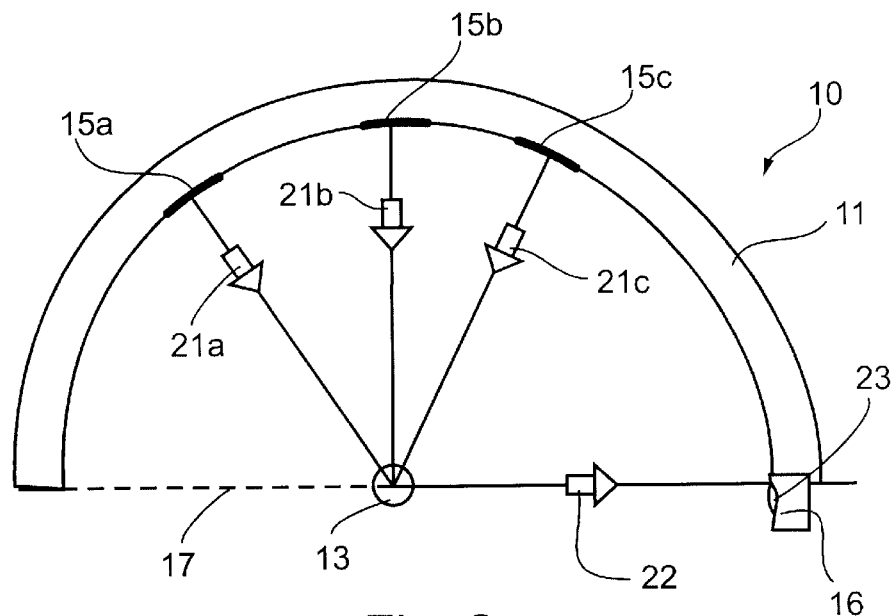
FIG. 2 is a diagram of the system of FIG. 1 functioning without interference from a skull.

For purposes of illustration, FIG. 2 shows the system 10 detached from the patient's skull 14. For simplification, only three of the transducer elements, 15A, 15B and 15C, are shown in FIG. 2. The transducer elements 15A–C are pulsed, with the energy pulses from elements 15A, 15B and 15C denoted as respective vectors 21A, 21B and 22C. Without the distortion produced by the non-uniform thickness of the skull 14, the desired phase and amplitude of the pulses 21A–C are easily determined so the pulses will arrive in phase, and thereby constructively interfere, at the focal zone 13. In this instance, there will be a concentrated degree of reflectance of the pulsed beam at the focal zone 13 detected by the detector 23 along its line-of-sight axis 17. The amount of time required for the detector 23 to receive the reflected beam portions or "reflectance" 22 from the respective pulses 21A–C can be exactly predicted, since the speed of sound in tissue (about 1540 m/sec), and the distance from the respective transducer elements 15A, 15B and 15C to the detector 23 are both known. Thus, for a given pulse 21A–C emitted by transducer elements 15A–C, the detector 23 receives the reflected signal intensity along the length of its line-of-sight axis 17 passing through the focal zone 13 as a function of time.

Figure 3:
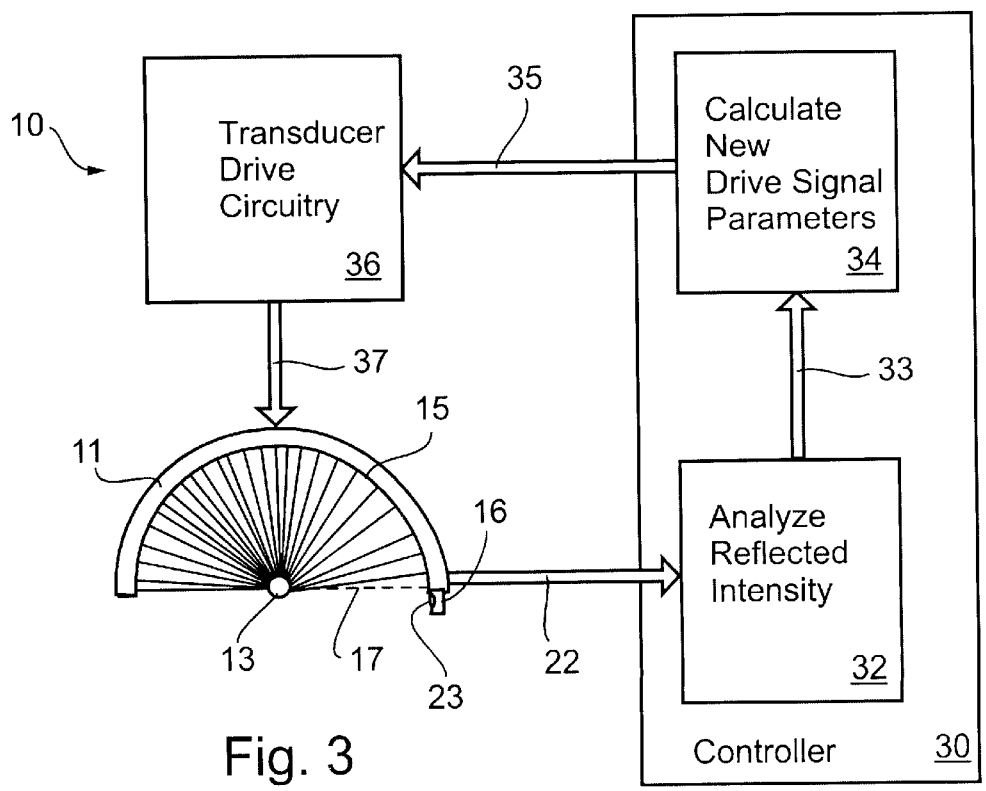
FIG. 3 is a simplified schematic drawing of a closed-loop control system for the system of FIG. 1.

With reference also to FIG. 3, the received signal from the detection probe 16 is recorded and analyzed (designated by a functional box 32) by a system controller 30. The controller 30 may comprise one or more of a microprocessor, micro-controller, central processing unit (CPU), arithmetic logic unit (ALU), co-processor, application specific integrated circuit (ASIC), neural network, firmware, software, and/or any other type of control unit. The controller 30 translates the recorded times into distances, e.g., by a simple software algorithm. The controller 30 is thus able to determine the reflected intensity of the pulsed beam 21 as a function of location along the line-of-sight axis 17 of the detector 23 through the focal zone 13.

As explained in greater detail below, the reflected intensity data 33 is used to calculate adjusted transducer drive signal parameters (designated by the functional box 34) for a next pulse cycle. The drive signal parameters 35 are provided to the transducer drive circuitry 36, which generates respective sinus drive signals 37 for energizing the respective transducer elements 15. Details of preferred drive and control circuitry for operating a phased-array focussed ultrasound system are provided in U.S. Patent Application Ser. No. 09/724,611, entitled, "Systems and Methods for Controlling a Phased Array Focused Ultrasound System", filed on Nov. 28, 2000, which is fully incorporated by reference.

Referring again to FIG. 2, in accordance with a general aspect of the invention, the reflected intensity 22 of the pulsed beam 21 can be used to focus the beam 12 transmitted through a skull of non-uniform thickness 14, i.e., for calibrating the individual phase shift and/or amplitude of the individual transducer elements to account for the skull 14. For example, focussing of the beam 12 may be performed by adjusting the respective phase shift and/or amplitude of one or more of the individual transducer elements 15 after each pulse 21 in order to maximize the intensity of the reflected signal in the focal zone 13, i.e., along that portion of the detector transducer line-of-sight axis 17 passing through the focal zone 13. The phase shift and amplitude of each transducer element 15 may be individually tuned to provide a maximum reflected intensity 22. Because of the relatively short pulse duration, e.g., one $\mu$ sec for a beam frequency of 1 MHz), this can be accomplished relatively quickly, even for a relatively large transducer array. In one embodiment, the focussing process is carried out as follows:

1. Start a pulse mode cycle using the best available approximation for the transducer element phase shifts and amplitudes.

2. Point the detector 23 in the direction of the geometric center of the spherical transducer array 13.

3. Calculate the point in time in the received signal at the detector 23 that corresponds to reflectance 22 received from the geometric center of the transducer array 13. All ensuing steps will be intended to maximize the intensity at this point, i.e., wherein only readings from this point are used.

4. Vary the phase shift and/or amplitude of a single transducer element 15 for a subsequent number of pulses to determine the phase value resulting in the detector 23 receiving a maximum reflectance signal 22. Thereafter, set the phase shift of the respective transducer element 15 with this determined value. Notably, the variation of a single transducer element 15 in a large transducer array 11 may have very little effect on the detector reading. To enhance this effect, the intensity of the currently tuned element 15 should be considerably increased, e.g., with the intensity of the emitted ultrasound from this element 15 equal to the sum of all other elements.

5. Repeat procedure sequentially for each element 15 of the transducer array 11. Because the later tuning of some elements may effect the "optimum" phase setting of an already tuned element, it may be helpful to repeat the tuning cycle for all elements 15 several times, i.e., as an iterative process, until the tuned settings converge.

Notably, the accuracy of determining the location of the geometric center of the focal zone 13 is not very critical. In the actual treatment, the real location will be determined by e.g. the MRI temperature mapping.

A variation of the above-described focussing process may be performed by varying the phase shifts of the respective transducer element 15 in a closed-loop iterative process, until the boundaries of the "de-focussed" zone 18 approach those of the desired focal zone 13.

In an alternative embodiment, the phases and/or amplitudes of the transducer elements 15 are adjusted to maximize the intensity of the reflectance signal 22 at the point that initially has the highest intensity signal, regardless of where the point is. In this embodiment, it is not necessary to locate the boundaries of the "de-focussed" zone 18, but just to identify a point of maximum intensity and then to optimize the intensity at this same point by the above-described iterative process. The focal point (or zone) of the beam 12 may then be moved to the desired position through conventional beam steering techniques, once the aberrations in skull thickness are compensated for. Such movements are accomplished by changing the relative phases of the transducer elements 15 according to independently known calculations, which do not generally affect the degree of focus at the initial position or the selected position.

Figure 4A:
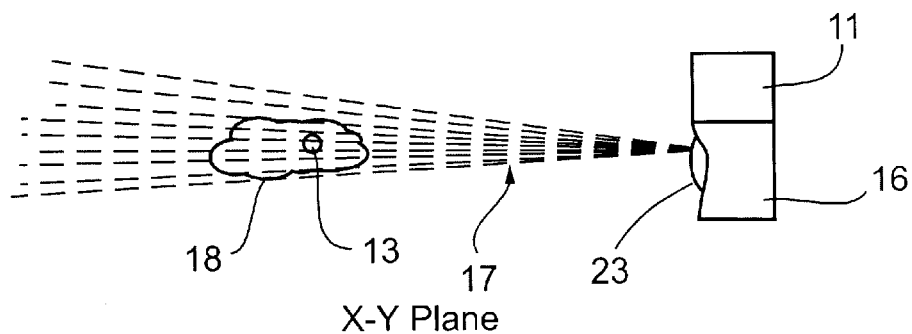
FIGS. 4A–B are cross-sectional views of one embodiment of the system of FIG. 1 taken along x-y and x-z planes.
Figure 4B:
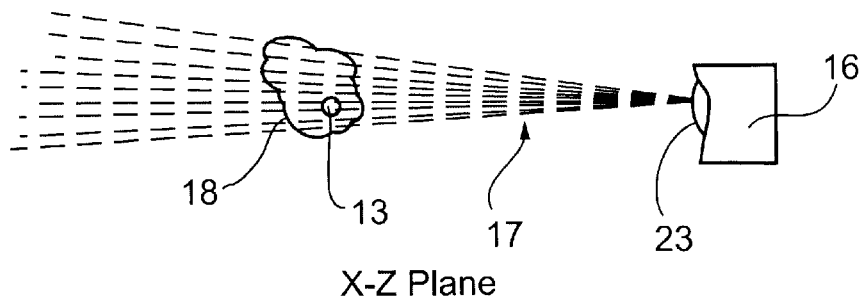

Referring to FIG. 4, a two-dimensional, or three-dimensional distribution of reflected intensities of the beam 12 may be obtained by sweeping the line-of-sight axis 17 of the detector 23 in both a x-y plane, and a x-z plane, in the general area of the intended focal zone 13. Movement of the line-of-sight axis of the detector 23 is preferably controlled by the controller 30, e.g., by using a small piezoelectric motor to rotate the relative transducer orientation within a given range of movement in at least one, and preferably two degrees of freedom. As is known in the art, in order to get a two-dimensional image, the detector must be rotated in one degree of freedom. For a three-dimensional image, the detector must either be rotated in two degrees of freedom, or rotated in one degree of freedom and one translation.

For example, the line-of-sight axis 17 can be repeatedly moved some increment in a first x-y plane, as is typical in ultrasound imaging, to create a fan of axes and a two-dimensional distribution of the measured intensities. The entire detection probe 16 can be tilted or moved out of this plane along a z-axis to evaluate intensities in other planes, thereby obtaining a three-dimensional distribution of the measured intensities in the area of the intended focal zone 13. Starting from the 3-D reflectance intensity information of the "de-focussed" zone 18, one can commence the process of varying phases to increase the intensity in intended focal volume 13.In some cases it may be preferable to start the detection and mapping process with the best available approximation of the transducer element phases.

Figure 5:
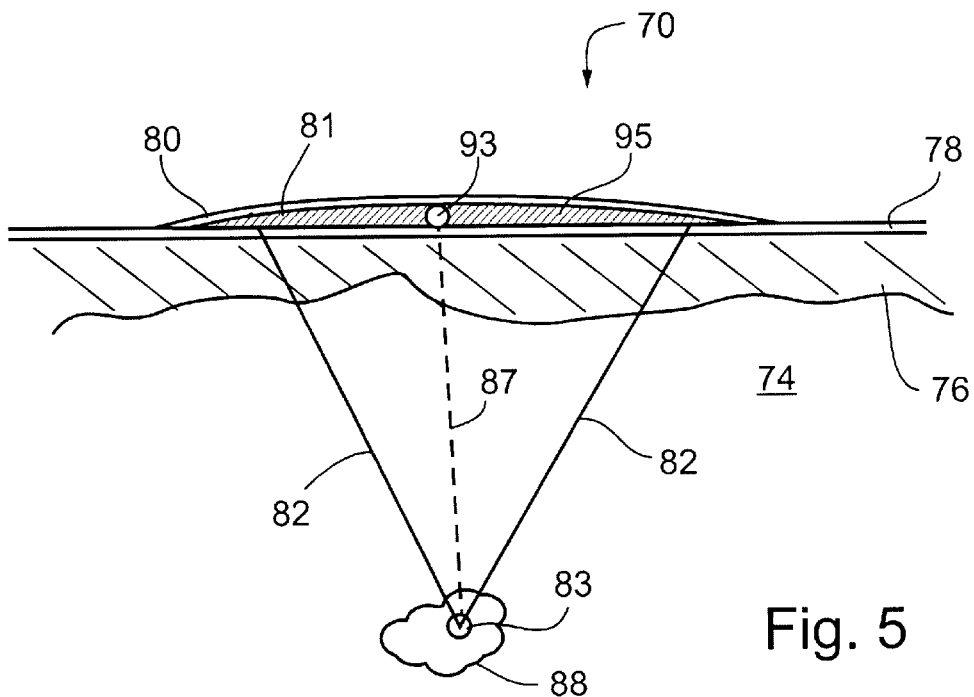
FIG. 5 is a cross-sectional view of a system for delivering a focused ultrasound energy beam from outside the body to a target tissue area underlying a non-uniform fat layer and detecting the intensity of reflected portions of the beam along an axis through an intended focal zone.

For purposes of further illustration of the scope of the present invention, FIG. 5 depicts a system 70 employing a phased-array transducer 80 for delivering a focused ultrasound energy beam 82 from outside a patient's body to a muscle tissue region 74 underlying a non-uniform fat layer 76. The transducer 80 comprises a phased array of individually controllable transducer elements 81, each configured to transmit acoustic wave energy through the patient's skin 78 to a target focal zone 83 in the muscle tissue 74, the collective wave energy forming an energy beam 82.

As with the above-described trans-cranial system 10, the acoustic wave energy transmitted from each individual transducer element 81 may be offset in phase and/or amplitude from the others in order to change the location, shape and/or orientation of the focal zone 83. An acoustically conductive fluid or gel 95 is preferably introduced between the inner face of the transducer 80 and the exterior of the patient's skin 78 in order to prevent any acoustically reflecting air gaps. The system 70 may be operated in continuous mode, pulsed mode, or in some selected sequence of both continuous and pulsed mode operation.

Prior to initiating any high intensity beam transmission to the desired focal zone 83, the respective phase shifts and amplitudes of the individual transducer elements 85 must be calibrated to account for aberrations in thickness of the fat layer 76. Once properly focussed, the energy waves will converge at the focal zone 83 in phase, creating a constructive interference pattern with most all of the beam energy concentrated in the focal zone 83.

However, if the phase shifts and/or amplitudes of the individual transducer elements 81 are not properly calibrated to account for the fat layer thickness aberrations, the energy beam 82 will be defocused, appearing as a larger volume of non-uniform intensity 88.

Focussing of the beam 82 is preferably performed at low energy levels, so as to avoid harming any of the muscle tissue 74 before the beam 82 is properly focussed. Further, the focussing process is preferably performed after an initial approximation of the phase shifts of the individual transducer elements 81 is determined. To focus the energy beam 82, the system 70 employs a detector transducer 93. Notably, alternate embodiments may employ more than one detector transducer. The detector 93 is positioned in a fixed coordinate position relative to the transmitting transducer elements 81, and is focussed in the direction of the intended focal zone 83. As with the detector 23 in system 10, detector 93 preferably has a relatively long and narrow focal volume, i.e., practically a line or very thin tube, such that its cross-section passing through the intended focal zone 83 may be as small as 1 mm. In this manner; the detector 93 will receive reflections of the beam 82 transmitted through the fat layer 76 and skin 78 from points along a relatively well defined axis 87, which passes through the intended transducer focal zone 83.

Focusing of the beam 82 in system 70 is performed in substantially the same way as focussing beam 12 in system 10, e.g., the transducer elements 81 are energized (preferably in a pulsed mode) and the detector 93 receives the reflected signal intensity of the beam 82 along the length of its line-of-sight axis 87 passing through the intended focal zone 83 as a function of time. The received signal is then decoded to determine the reflected intensity of the (pulsed) beam 82 as a function of location along the line-of-sight axis 87 of the detector 93 through the intended focal zone 83. The reflected intensity data is then used to adjust transducer drive signal parameters for a next pulse cycle in the same manner as for the above described trans-cranial system. While embodiments and implementations of the subject invention have been shown and described, it should be apparent that many more embodiments and implementations are within the scope of the subject invention.

For example, while the above-described embodiments are directed to a focussed ultrasound treatment (i.e., thermal ablation) system, the principles of the invention (i.e., focussing through a non-uniform tissue medium) are equally applicable to an ultrasound imaging system.

Accordingly, the invention is not to be restricted, except in light of the claims and their equivalents.

What is claimed is:

1. A system for delivering an energy beam transmitted through a non-uniform tissue medium in a body, comprising:
   a transmitter comprising a plurality of transmitting elements configured to deliver respective energy waves from outside the body through the non-uniform tissue medium to a target tissue area in the body, the energy waves collectively comprising the energy beam;
   a detector having a known position relative to the transmitting elements, the detector configured to receive a signal representing the intensity of reflected portions of the beam along a line-of-sight axis within the body; and
   a controller coupled to the transmitter and detector, the controller configured to calculate the location and intensity of the reflected beam portions along the axis based on the timing of the received signal, the controller further configured to adjust transmission parameters of one or more of the transmitting elements based on the location, intensity, or both, of the reflected beam portions.

2. The system of claim 1, wherein the beam is a focused ultrasound beam.

3. The system of claim 2, wherein the transmitter is a phased array ultrasound transducer.

4. The system of claim 1, wherein the non-uniform tissue medium is a skull, and wherein the detector receives the signal representing a reflected portion of the beam through a portion of the skull that does not cause significant distortion of the received signal.

5. The system of claim 4, wherein the portion of the skull through which the detector receives the signal is in the temple region, eye region, or the base of the skull.

6. The system of claim 1, wherein the non-uniform tissue medium is a skull, and wherein the detector receives the signal through a portion of the skull which distorts the signal in a predictable and calculable manner, and wherein the controller is configured to process the received signal by compensating for the predictable and calculable distortion.

7. The system of claim 1, wherein the frequency of the received signal is an integer multiple of the frequency of the energy waves transmitted by the transmitting elements, and wherein the integer is greater than one.

8. The system of claim 1, wherein the line-of-sight axis of the detector is movable in at least one plane relative to an axis normal to the detector.

9. The system of claim 8, wherein the line-of-sight axis of the detector is movable to receive signals representing intensities of reflected portions of the beam for a two-dimensional slice or three-dimensional volume within the body.

10. The system of claim 9, wherein the controller is configured to determine a location within the two dimensional slice or three dimensional area having a greatest calculated reflected beam intensity, and wherein the controller is further configured to adjust the transmission parameters of the one or more of the transmitting elements based on maximizing the calculated reflected beam intensity at the determined location.

11. The system of claim 1, wherein the transmission parameters comprise a relative phase shift, amplitude, or both of the energy waves transmitted by the respective transmitting elements.

* * * * *